United States Patent [19]

Baker, Jr.

[11] Patent Number: 5,743,263
[45] Date of Patent: Apr. 28, 1998

[54] PULSE OXIMETER USING A VIRTUAL TRIGGER FOR HEART RATE SYNCHRONIZATION

[75] Inventor: Clark R. Baker, Jr., Castro Valley, Calif.

[73] Assignee: Nellcor Puritan Bennett Incorporated, Pleasanton, Calif.

[21] Appl. No.: 539,579

[22] Filed: Oct. 5, 1995

Related U.S. Application Data

[63] Continuation of Ser. No. 134,572, Oct. 8, 1993, Pat. No. 5,485,847.

[51] Int. Cl.$^6$ ............................................. A61B 5/00
[52] U.S. Cl. ............................................. 128/633
[58] Field of Search ........................ 128/632, 633, 128/666, 665, 670, 700, 690, 668, 672, 691; 356/39–42

[56] References Cited

U.S. PATENT DOCUMENTS

| | | | |
|---|---|---|---|
| 3,916,878 | 11/1975 | Courtin et al. | 128/698 |
| 4,911,167 | 3/1990 | Coreman et al. | 128/633 |
| 4,928,692 | 5/1990 | Goodman et al. | 128/633 |
| 4,960,126 | 10/1990 | Conlon et al. | 128/633 |
| 5,099,841 | 3/1992 | Heinonen et al. | 128/633 |
| 5,309,908 | 5/1994 | Friedman et al. | 128/633 |
| 5,485,847 | 1/1996 | Baker, Jr. | 128/632 X |

FOREIGN PATENT DOCUMENTS

0 442 011 A1  8/1991  European Pat. Off. .

*Primary Examiner*—Jennifer Bahr
*Assistant Examiner*—Samuel Gilbert
*Attorney, Agent, or Firm*—Townsend and Townsend and Crew

[57] ABSTRACT

The present invention provides an improved method and apparatus for more accurately calculating and measuring vital information such as oxygen saturation and pulse rate when an ECG signal is not available. Instead of using an ECG R-wave as a trigger to overlay optical pulses, a virtual trigger is generated based on the heart rate and used to overlay optical pulse data. The optical information from a number of periods is added together, with the beginning of each period being determined by the issuance of the virtual trigger. In this way, the maximum and minimum of the optical signal should be lined up with each other in each period and added together to give a cumulative maximum and minimum. This enables precise identification of the maximum and minimum of the signal, and thus allows calculation of the oxygen saturation at that point.

14 Claims, 10 Drawing Sheets

PULSE OXIMETER USING A VIRTUAL TRIGGER FOR HEART RATE SYNCHRONIZATION

This is a Continuation of application Ser. No. 08/134,572, filed Oct. 8, 1993 now U.S. Pat. No. 5,485,847.

BACKGROUND OF THE INVENTION

The invention relates generally to a non-invasive pulse oximetry system and specifically to an improved method and apparatus for determination of blood constituents using a heart rate signal from a remote monitor.

Pulse oximeters typically measure and display various blood characteristics including but not limited to blood oxygen saturation of hemoglobin in arterial blood, volume of individual blood pulsation supplying the flesh, and the rate of blood pulsations corresponding to the heartbeat of the patient. This is typically done by detecting the amount of red and infrared signals absorbed by oxygen in the blood. A problem with non-invasive pulse oximeters is that the pulse rate which appears in the oximeter signal may be subject to irregular variants that interfere with the detection of blood flow characteristics including but not limited to motion artifact. Motion artifact can be caused by the patient's muscle movement proximate to the oximeter sensor and/or movement of the sensor. In fetuses this can include labor, maternal breathing, and maternal motion. In adults, movement of the patient's finger, ear or other body part to which an oximeter sensor is attached, may cause spurious pulses similar to pulses caused by arterial blood flow. These spurious pulses, in turn, may cause the oximeter to process the artifact waveform and provide erroneous data. This problem is particularly significant with infants, fetuses, or patients that do not remain still during monitoring.

A second problem exists in circumstances where the patient is in poor condition and the pulse strength is very weak. In addition to poor patient condition, low pulse strength may also be due to the choice of sensor site. In continuously processing the optical signal data, it can be difficult to separate the true pulsatile component from artifact pulses and noise because of a low signal to noise ratio. Inability to reliably detect the pulsatile component in the optical signal may result in a lack of the information needed to accurately calculate blood constituents.

Figure 1:
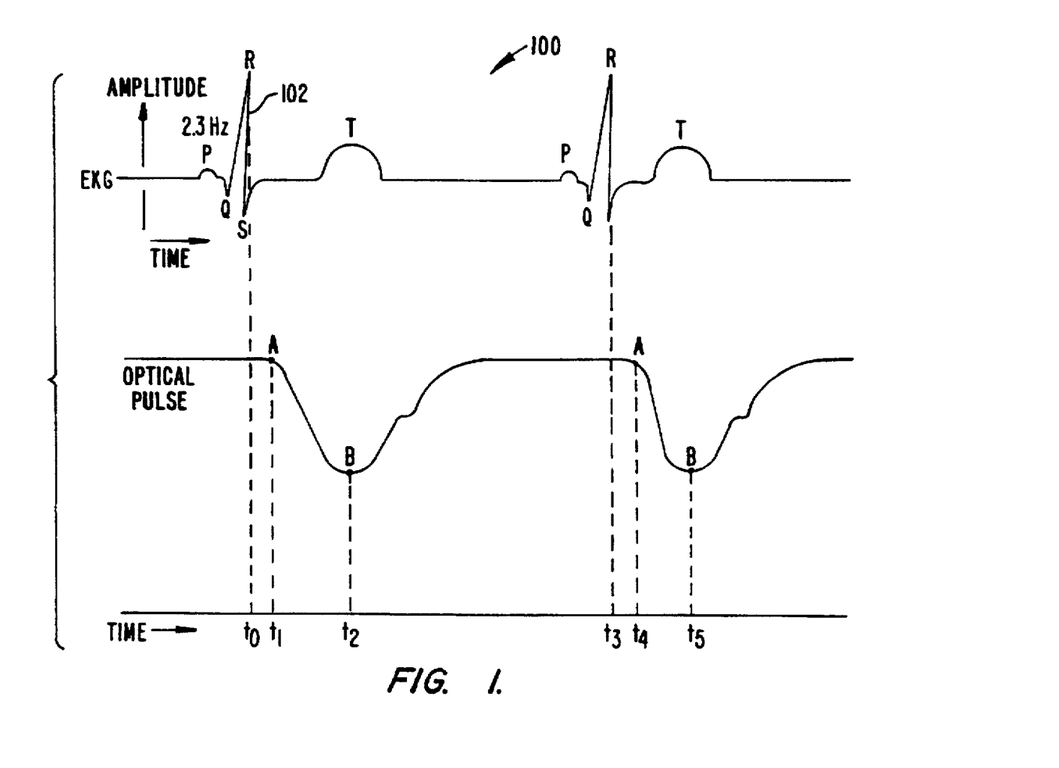
FIG. 1 illustrates a diagnostic ECG waveform.

U.S. Pat. No. 4,911,167 to Corenman et al. and U.S. Pat. No. 4,928,692 to Goodman et al. both describe a method and apparatus for increasing the accuracy of the pulse oximetry measurements using an electrocardiogram ("ECG") waveform. The ECG waveform 100 shown in FIG. 1 comprises a complex waveform having several components that correspond to electrical heart activity. The R-wave portion 102 of the waveform is typically the steepest wave, having the largest amplitude and slope, and may be used for indicating the timing of cardiovascular activity. The improved method described in U.S. Pat. Nos. 4,911,167 and 4,928,692, hereinafter referred to as the C-Lock process, refers to the use of the ECG signal to 1) gate data entries corresponding to a heart beat into a buffer, and 2) to trigger the search for the maximum and minimum values of the optical signals. The C-Lock process improves oximeter accuracy by using the ECG R-wave as a trigger to overlay optical pulses to cancel noise.

By synchronizing the optical signal to the occurrence of successive R-waves, it becomes possible to add the corresponding successive portions of a detected optical signal together so that the periodic information (optical pulses) corresponding to the arterial pulse in each portion of the detected optical signal add in phase. The optical information from a number of periods is added together, with the beginning of each period being determined by the detection of the R-wave. In this way, the maximum and minimum of the optical signal should be lined up with each other in each period and added together to give a cumulative maximum and minimum. This enables precise identification of the maximum and minimum of the signal, and thus allows calculation of the oxygen saturation at that point. Because aperiodic signals have different impulse shapes, duration, height, and relative time of occurrence within each portion, and are not synchronized with heart activity, they do not add in phase. Rather they add in a canceling manner whereby the weighted sum is spread across the relative time frame of the composite portion. Cancellation of the aperiodic signals cancels signal noise resulting in a cleaner optical waveform. This allows the oximeter to track the pulses more reliably and compute a more accurate blood oxygen saturation value with fewer dropouts.

Although the C-Lock process improves oximeter accuracy, an ECG signal is not always available. For example, to monitor fetal ECG heart activity, a scalp electrode is typically attached to the fetus. However, a large portion of deliveries in the United States and virtually all deliveries in Japan do not have access to fetal scalp electrode equipment. Instead, the fetal heart rate is monitored by external non-invasive means such as doppler ultrasound. Although the doppler ultrasound equipment provides heart rate information, it does not output an ECG waveform. Because no ECG waveform is available, the C-Lock process has no periodic R-wave trigger to synchronize optical pulses. Thus, the C-Lock process cannot be used to improve the accuracy of the blood oxygen saturation calculation where an ECG waveform (a fetal scalp electrode) is not available.

A method and apparatus for improving the accuracy of the blood oxygen saturation calculation in an oximetry system where a direct contact ECG waveform signal is not available and which decreases susceptibility to motion artifact is needed.

SUMMARY OF THE INVENTION

The present invention provides a method and apparatus for implementing the C-Lock process described in U.S. Pat. Nos. 4,911,167 and 4,928,692 to more accurately calculate and measure vital information such as oxygen saturation and pulse rate when an ECG signal is not available. In the present invention, the ECG R-wave is not used as a trigger to overlay optical pulses. Instead, a virtual trigger is generated and is used as a trigger to overlay optical pulse data gathered for a predefined pulse period following the virtual trigger. The apparatus and method of the present invention can be applied to any periodic physical activity that is measured and which needs to be synchronized to another signal of the same frequency for processing data.

Applicants have discovered that as long as the occurrence of the virtual trigger corresponds to the heart rate, it can be arbitrarily placed anywhere within the heart rate period. Thus, the timing of the virtual trigger is selected arbitrarily, and then its frequency is adjusted in accordance with a heart rate measured by a heart rate monitor.

The heart rate monitor need only provide the frequency of the heartbeat, and can be obtained from a pressure sensitive pulse monitor or a sound sensitive monitor which can detect the fetus' heartbeat, for instance, from the outside the mother's body. This eliminates the need to generate the specific waveform of electrical signals through an EKG monitor.

The use of a virtual trigger anywhere within the period of the heart rate will work because the combination of oximeter signals from multiple periods is actually a frequency-dependent filtering operation. Thus, an arbitrary virtual trigger will work since it is the frequency which is crucial, not the placement of the trigger within the period.

Oximetry system software typically calculates the blood oxygen saturation level based on the maximum and minimum optical signal values collected during a single pulse. The present invention recognizes that if the heartbeat is regular, the pulse period during which optical signal data is collected is equal to sixty seconds divided by the heart rate (time period for a single pulse). Because a maximum and minimum optical signal value occur during the pulse period, an arbitrary (virtual) trigger can be generated and the maximum and minimum optical signal values will be found during the pulse period following the virtual trigger.

Substitution of the R-wave trigger with a virtual trigger for C-Lock implementation is possible since the C-Lock process is dependent on the frequency of the optical signal and not the specific phase relationship between the ECG R-wave trigger and the optical signal. Thus, if the heart rate is regular from beat to beat and the timing of a virtual trigger is known along with the heart rate, the exact timing of the next several triggers to overlay optical signals can be predicted with a high degree of likelihood.

Replacing the R-wave trigger with a virtual trigger as required by the present invention eliminates the need for an ECG monitor. In addition, because the ECG R-wave is not used to determine the time period for overlay of optical pulses, the computation of the derivative of the ECG signal to detect the R-wave is eliminated, decreasing the computation time necessary for determining blood oxygen saturation. The present invention works best for patients where the heart rate does not vary quickly. Thus, the invention would be very useful for fetal monitoring, but would not be as accurate for the patient with arrhythmia, where the heart rate varies significantly over a short time.

A further understanding of the nature and advantages of the invention may be realized by reference to the remaining portions of the specification and the drawings.

DESCRIPTION OF THE DRAWINGS

FIGS. 3, 3A, 3B, 3C, 3D, and 3E are flow charts illustrating the software implementation according to the present invention.

DESCRIPTION OF THE SPECIFIC EMBODIMENTS

The present invention provides a method and apparatus for implementing the C-Lock process to more accurately calculate and measure vital information such as oxygen saturation when an ECG signal is not available. The C-Lock process as described in U.S. Pat. Nos. 4,911,167 and 4,928,692 refers to the use of the ECG signal to 1) gate data entries corresponding to a heartbeat into an ensemble averaging buffer and 2) to trigger the search for maximum and minimum values of the optical signals (red and infrared in the preferred embodiment). In the present invention, no ECG signal is available. Thus, the R-wave portion of the ECG signal cannot be used as a trigger to synchronize the optical signal.

Instead, the present invention uses a virtual trigger generated in software as a trigger to overlay optical pulse data. In one embodiment, blood oxygen saturation data is based on the maximum and minimum optical signal values collected during a single pulse. Thus if the heart beat is regular the pulse period during which optical signal data is collected is equal to sixty seconds divided by the heart rate (time period for a single pulse). Because a maximum and minimum optical signal value occurred during the pulse, an arbitrary (virtual) trigger can be generated and the maximum and minimum optical signal values will be found during the pulse period following the virtual trigger. Alternately, any portion or all of the optical signal wave form could be used for the analysis, instead of the maximum and minimum.

The virtual trigger is used to synchronize the optical signal so that it becomes possible to add corresponding successive portions of the detected optical signal together so that the periodic information in the optical signal corresponding to the pulse will add in phase. Any aperiodic information that may be present in portions of the detected optical signals typically differ in pulse shape, duration, height, and relative time of occurrence within each portion and are not synchronous with the heart activity and therefore do not add and phase. Rather, they add in a cancelling manner whereby their weighted sum is spread across relative time frame of the composite signal.

Figure 2A:
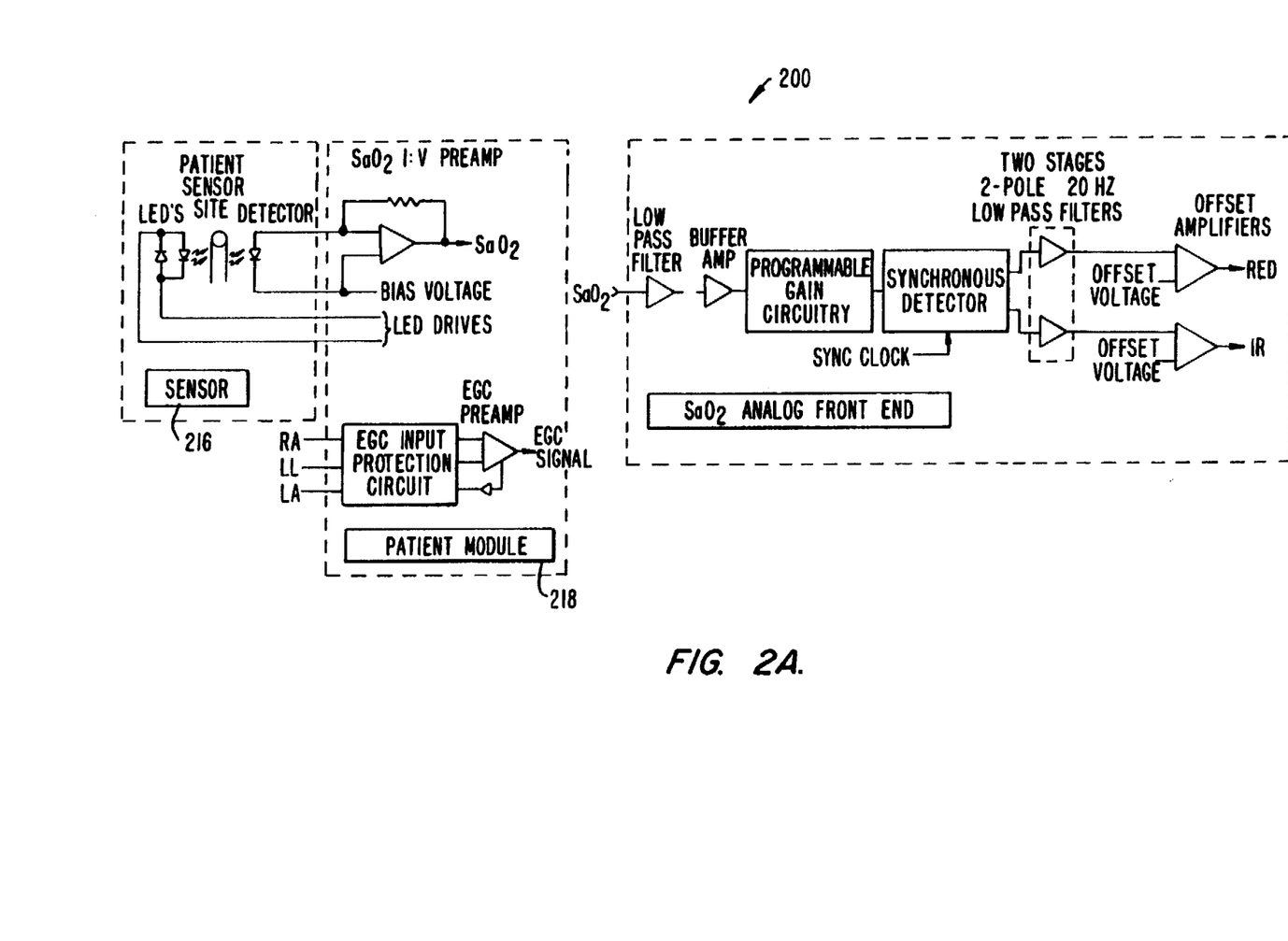
FIGS. 2A and 2B are block diagrams of the apparatus for implementing the C-Lock process when no ECG waveform is available according to the present invention.
Figure 2B:
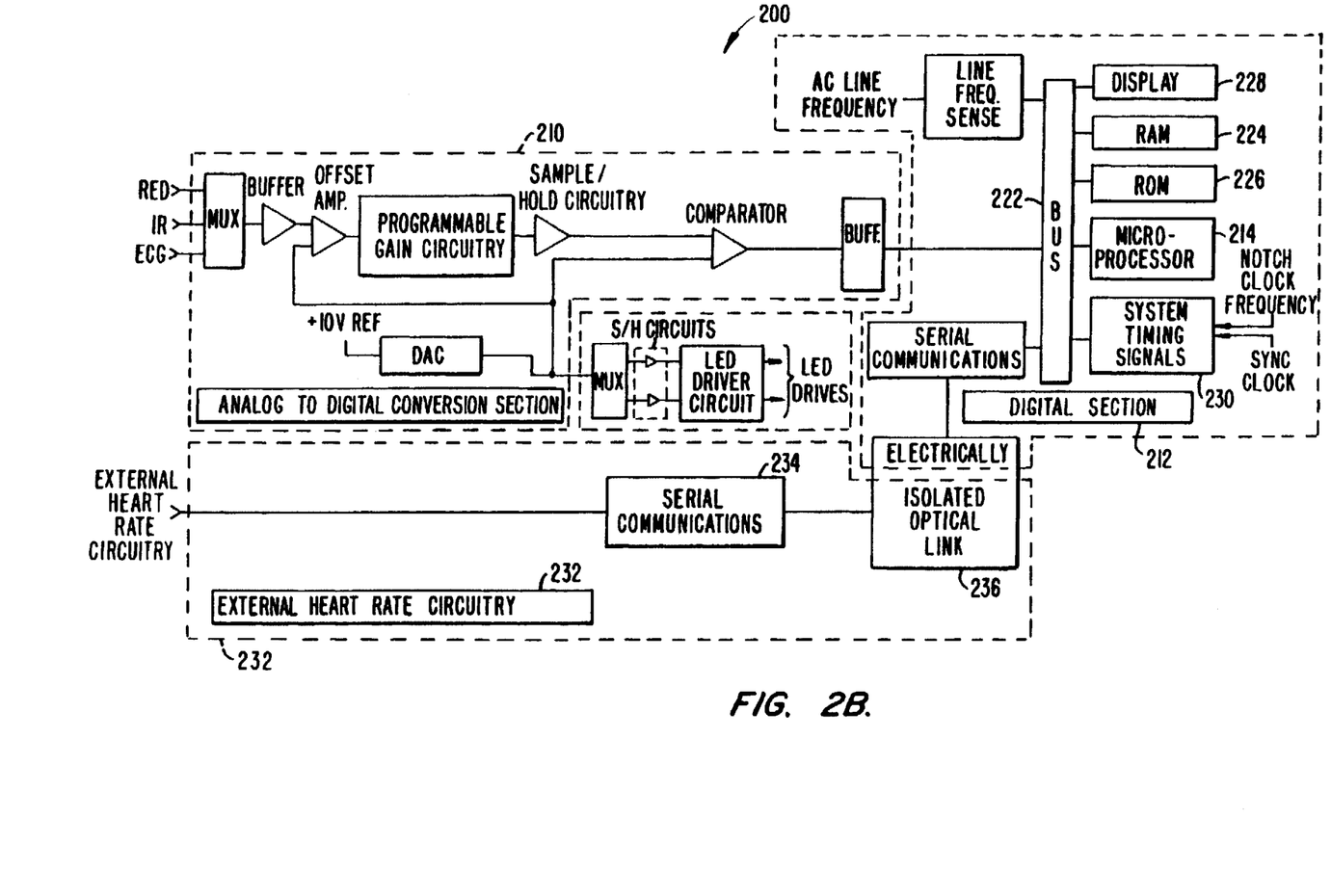

FIGS. 2A and 2B are block diagrams of the apparatus according to the present invention which implements the C-Lock process using an external heart rate signal. The pulse oximetry system 200 is typically comprised of an analog-to-digital conversion section 210 and a digital signal processing section ("DSP") 212 including the software for driving the microprocessor 214, which processes the digitized optical signals and the heart rate signal to determine the oxygen saturation of hemoglobin in arterial blood. The pulse oximetry system 200 is further comprised of a plethysmography sensor 216 for detecting optical signals including periodic optical pulses, a patient module 218 for interfacing the sensor 216 with the saturation analog front end circuit 218 and a saturation analog circuit 218 for processing the detected optical signals into separate red and infrared channels that can be digitized. In addition, the pulse oximetry system 200 includes an LED drive circuit 220 for strobing the red and infrared LED and the sensor 100 at the proper intensity to obtain a detected optical signal that is acceptable for processing, and various regulated power supplies (not shown) for driving or biasing the associated circuits, as well as the ADC 210 and DSP 212, from line current or storage batteries. The associated elements are straightforward circuits providing specified functions which are well within the skill of an ordinary engineer to design and build.

Referring to FIG. 2B, the digital signal processing unit 212 controls all aspects of the signal processing operation including the signal input and output and intermediate processing. The apparatus includes a microprocessor 214 and its associated support circuitry including a data bus 222.

random access memory (RAM) 224, read only memory (ROM) 226, a conventional LED display device 228 (not shown in detail), system timing circuit 230 for providing the necessary C-Lock synchronization and notch filter frequency signals. In the preferred embodiment, the values corresponding to the detected optical signals are stored in the RAM 224.

FIGS. 3A, 3B, 3C, 3D, and 3E show the flowcharts for the software implementation of the preferred embodiment of the present invention. The applications software running on the microprocessor 214 is used to process the detected optical signals, to generate the virtual trigger and to determine the pulse period and blood flow characteristics. In the preferred embodiment, the microprocessor 214 is a model 80386 microprocessor, manufactured by Intel Corporation, Santa Clara, Calif. Software Appendix A sets forth the program implementing the flow charts of FIGS. 3A–3E.

The pulse oximetry system for implementing the C-Lock process when no ECG waveform is available includes a heart rate monitor. If the heart rate is obtained from an external monitor for use in triggering C-Lock, the heart rate obtained must be accurate. The heart rate may be obtained from a digital interface. A digital interface requires a digital connection to the external monitor (RS232) and support of communications protocols for multiple brands of heart rate monitors. Currently available fetal heart rate monitors include the HP 8040A currently available from the Hewlett Packard Corporation, Palo Alto, Calif. and the 115 currently available from Corometrics Corporation. If the heart rate is obtained from analog outputs, it is important that the oximeter system read the analog value accurately and be set for the right scaling. The scaling typically varies according to the brand of heart rate monitor used.

Typically the pulse oximeter system 200 is equipped with an external heart rate circuit 232. The mainline operating system controlling the operation of the oximeter receives an interrupt when the external heart rate monitor circuit 232 detects a heart rate signal. On receipt of the interrupt, a message is sent across the isolated optical data transmission path 234–236 to the microprocessor 214. The microprocessor 214 then indicates to the heart rate processing routines that an externally detected heart rate signal has occurred and the heart rate signal is passed to the Heart Rate Checking Routine.

Referring to FIGS. 3A–3E, interrupt programs control the collection and digitization of incoming optical and heart rate data. As particular events occur, various software flags are raised which transfer operation to various routines that are called from the Main Loop Processing routine shown in FIG. 3A. For example, the Main Loop Processing routine calls the Heart Rate Checking routine shown in FIG. 3B at step 352, calls a routine for checking the LED levels at step 354 to make sure that the proper level of light is being transmitted, looks for the presence of new data at step 356 and if there is new data, calls an ensemble averaging routine at step 357 and a standard pulse detection routine at step 358. The Main Loop Processing routine looks for pulse data at step 360 and passes such data to the pulse qualification routine (FIG. 3E) which calculates blood oxygen saturation at step 362. In addition, the Main Loop Processing routing runs various maintenance routines related to the oximeter functions not pertinent to the present invention (not discussed).

Figure 3A:
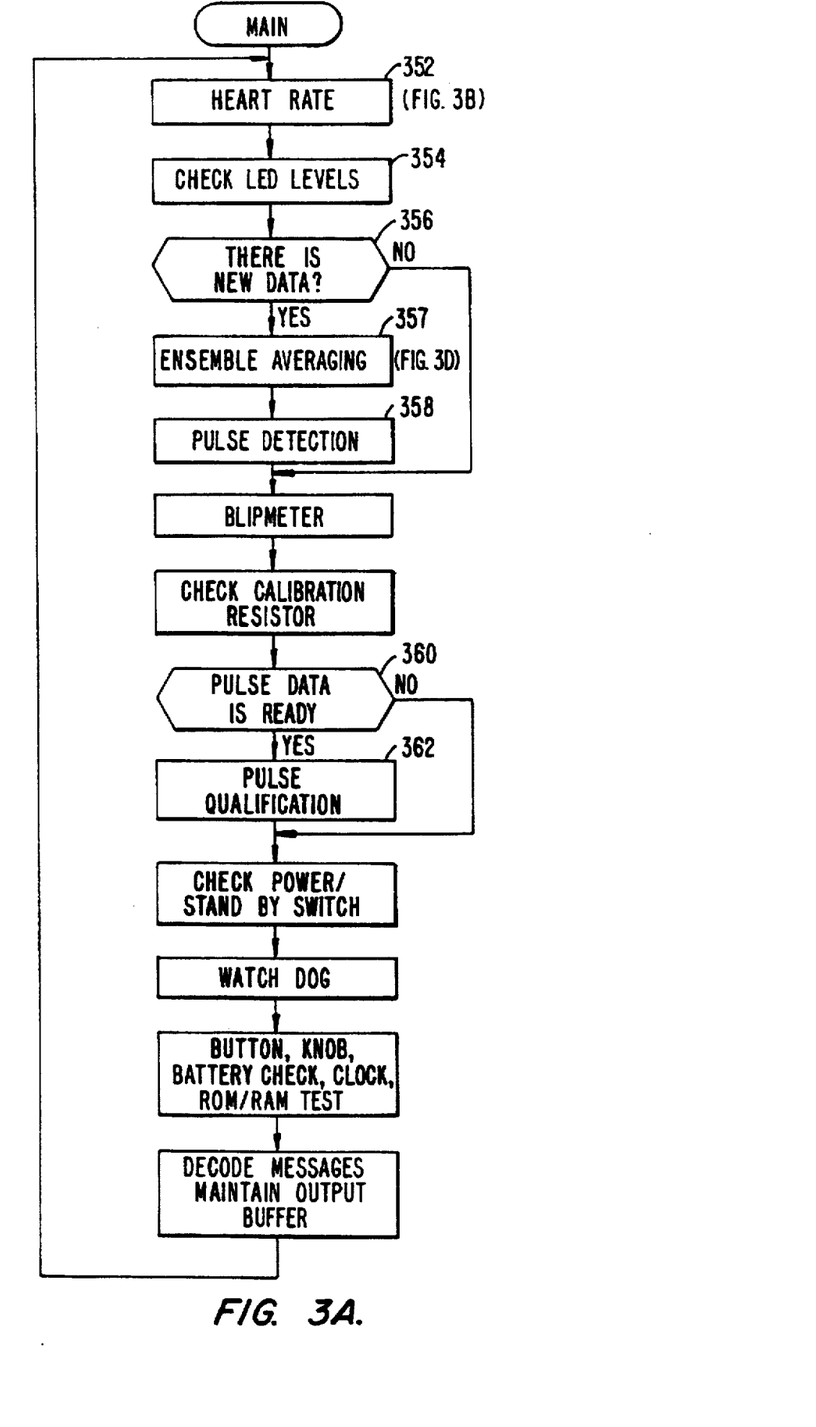
Figure 3B:
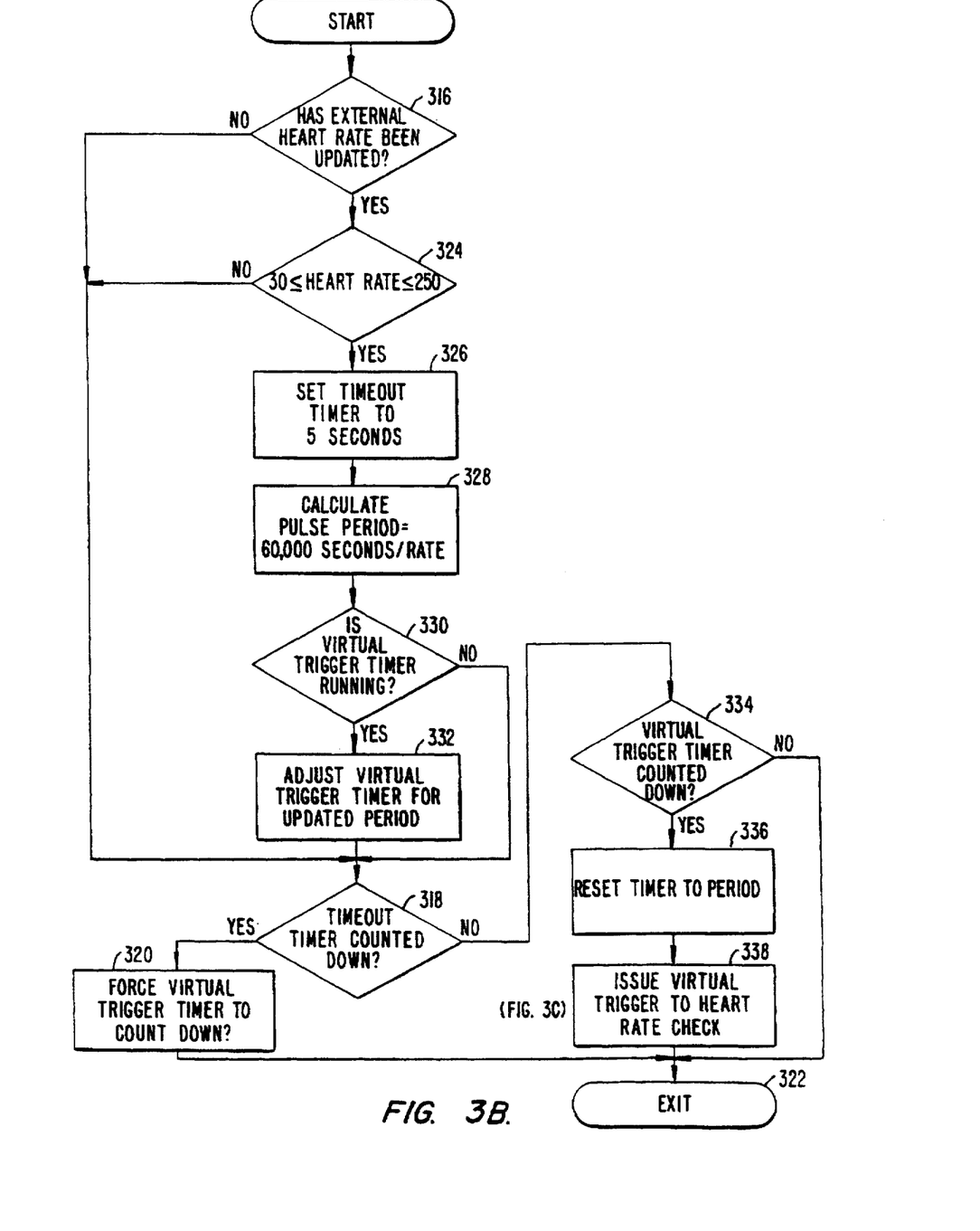
Figure 3C:
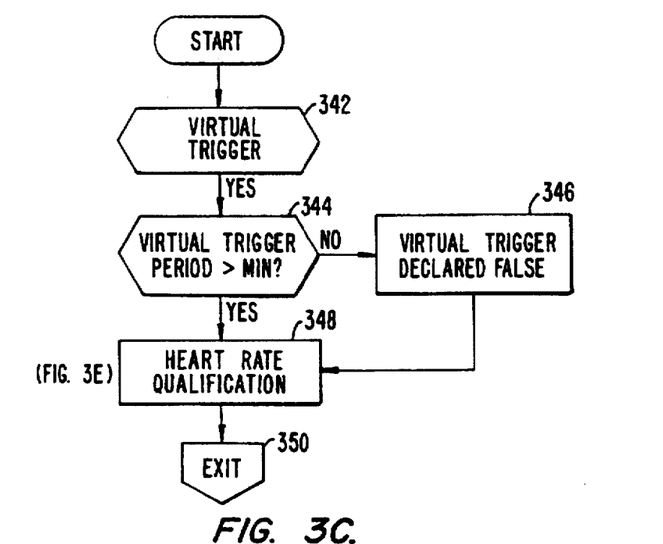
Figure 3D:
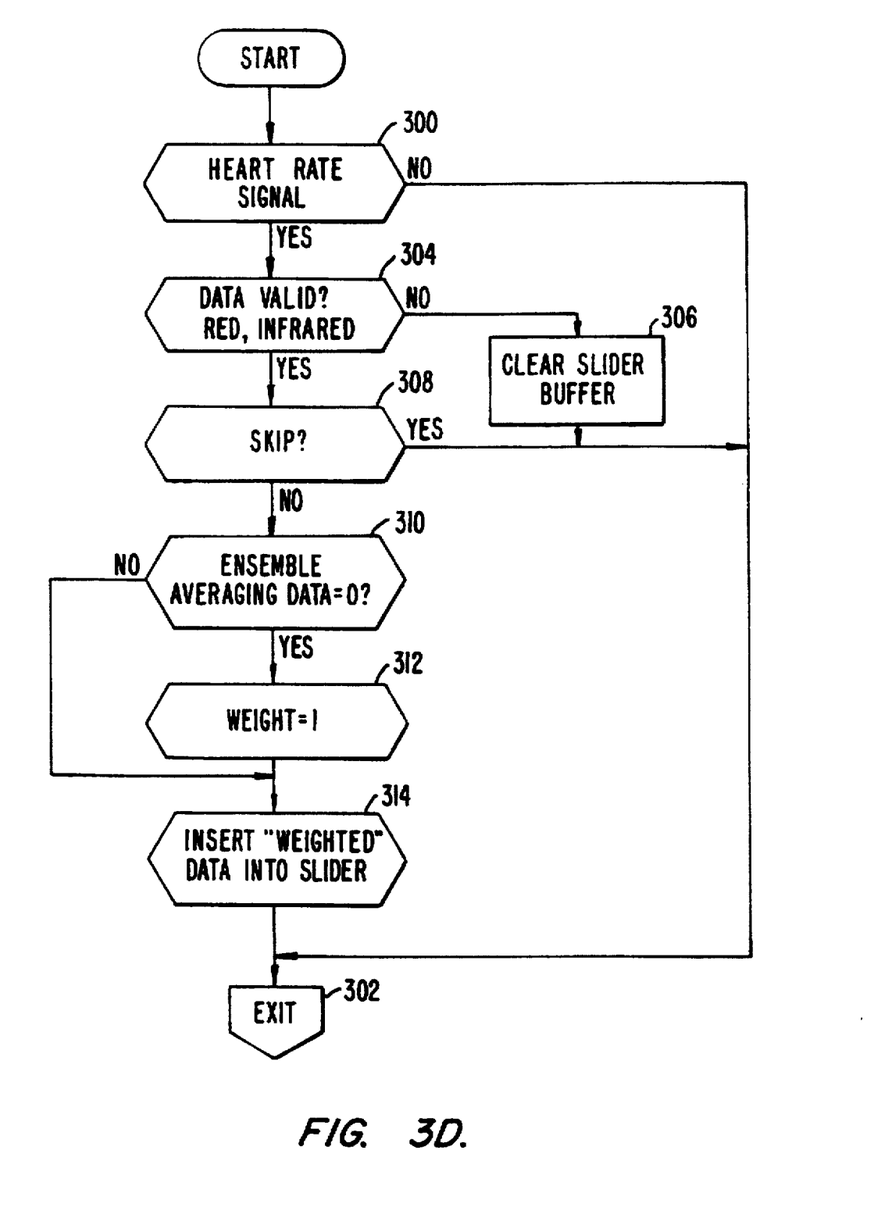

Referring to FIG. 3D, the ensemble averaging routine 357 of FIG. 3A processes each new digitized sample of the detected optical signal containing the optical pulse to create and maintain the enhanced composite red and infrared optical pulse waveforms, synchronized with the occurrence of the virtual trigger. The ensemble averaging routine first inquires whether there is a heart rate signal at step 300. If there is not, then the routine aborts to exit at step 302 to mainline operation. If there is a heart rate signal, then the ensemble averaging routine continues to check the validity of optical signal at step 304. If the digitized sample for either the red or infrared channels contains an invalid data point, the contents of the ensemble averaging buffer are erased at step 306 and the routine exited at step 302.

The ensemble averaging buffer is used to store red and infrared optical pulse data. If the microprocessor 214 does not receive or recognize a virtual trigger for a predefined period, typically greater than five seconds, the ensemble averaging buffer pointer is set to point to the last location and does not get incremented beyond that location. Time-out occurs when no virtual triggers occur for a predetermined period of time, typically, five seconds. After time-out occurs, the pulse detection routine is notified that heart rate synchronization is lost so that the blood oxygen saturation calculations are based only on the optical signals in the data buffer without implementation of the C-Lock process.

If the optical signal data is determined to be valid (step 304), then the ensemble averaging routine queries whether or not the data should be skipped at step 308. If the data is to be skipped, the ensemble averaging routine is exited at step 302. If not, the contents of the ensemble averaging buffer is weighted depending on the time interval that the data has been stored in the buffer. Before adding a weighting factor to the data, the ensemble averaging routine checks the ensemble averaging buffer to see if there is any existing data at step 310. If there is existing data, then the ensemble averaging routine calculates the new value for the composite optical signal. However, if the ensemble averaging buffer is empty, then the weighted value used in the ensemble averaging calculation is assigned a numerical value of 1 at step 312 and subsequent new data points will be weighted 100%. The ensemble averaging routine continues to calculate a new value for the composite optical signal at 314 until the occurrence of the virtual trigger corresponding to the following heartbeat.

To implement the ECG C-Lock process according to the description in U.S. Pat. No. 4,911,167 where an ECG signal is used to trigger data collection, the oximeter system relates the R-wave of the ECG signal to the red and infrared optical pulses. The R-wave portion of the ECG signal is typically the steepest wave having the largest amplitude and slope. Thus the R-wave can be determined by taking the derivative of the signal. Since the R-wave occurs once per heartbeat, the maximum and minimum optical signals for the heartbeat can be found between the occurrence of two consecutive R-wave events. The R-wave event is used to trigger input of red and infrared data into the ensemble averaging buffer for a single heartbeat.

FIG. 3B shows the flowchart for triggering data collection based on a heart rate signal instead of an ECG signal according to the present invention. In the present invention a heart rate signal is used to trigger the period during which optical signal data is collected. Because the R-wave event is no longer used as a trigger, the derivative calculation to determine the R-wave event illustrated in FIG. 9B of U.S. Pat. No. 4,911,167 is not necessary. Instead, a virtual trigger is used to trigger data collection according to the flowchart shown in FIG. 3B.

Referring to FIG. 3B, the Heart Rate routine first checks at step 316 whether the heart rate has been updated by checking the time when the last heart rate value was entered. If the heart rate has not been updated within a predefined time period, the timeout timer is checked at step 318 to see if it has counted down to zero. The timeout timer is used to prevent an old heart rate value from being used to generate a new virtual trigger. If the timeout timer has a value of zero (counted down), the heart rate value is old and the virtual trigger timer is forced to a count value of zero at step 320. After forcing the virtual trigger timer value to zero, the Heart Rate routine is exited at step 322. Forcing the virtual trigger timer to zero ensures that a new virtual trigger will be issued upon reentry into the Heart Rate routine.

If the heart rate value has been updated, the heart rate is checked in step 324 to determine if the heart rate is between 30 and 250 beats per second. If the heart rate is between 30 and 250 beats per second, the timeout timer is set to a period of five seconds in step 326. After the timeout timer is set in step 326, the pulse period is determined in step 328. Calculation of the blood oxygen saturation level is dependent on the maximum and minimum values of the optical signals during a single pulse. Thus the pulse period, the period for a single pulse, is the period during which data for a single oxygen saturation calculation is collected. The present invention recognizes that if the heartbeat is regular, the pulse period during which optical signal data is collected for a single oxygen saturation calculation is equal to sixty seconds divided by the heart rate.

After the pulse period is calculated, the virtual trigger timer is checked to see if it is running in step 330. Because a maximum and minimum optical signal value occur during the pulse period, an arbitrary (virtual) trigger can be generated and the maximum and minimum optical signal values will be found during the pulse period following the virtual trigger. If the heart rate is known and regular from beat to beat, consecutive virtual triggers are generated in software where each virtual trigger is separated by a pulse period. Thus, the timing of the next virtual trigger to overlay optical signals can be predicted with a high degree of likelihood.

The virtual trigger timer is checked in step 330 to see if it is set to a nonzero value (running). The function of the virtual trigger timer is to make sure that virtual trigger occurs at the proposed time. The timing of the virtual trigger is dependent on the pulse period. For example, if the heart rate is 120 beats/minute, the virtual trigger should occur every 500 milliseconds (60 sec÷120 beats/min.). However, if the heart rate is 180 beats/minute, the virtual trigger should occur more often, approximately every 333 milliseconds (60 sec÷180 beats/min).

If the virtual trigger timer is running, then the virtual trigger timer is adjusted for the newly updated pulse period in block 332. Next, the timeout timer is checked to see if it has counted down (reached a value of zero) in step 318. Alternatively, if the virtual trigger timer is not running, the virtual trigger timer is not updated and the timeout timer is checked in step 318 to see if it has counted down (reached a value of zero). In the preferred embodiment, the C-Lock process is implemented such that the timing of the virtual trigger is updated as soon as possible after the fetal heart rate is updated. Thus, if the heart rate changes, the timing of the next virtual trigger is adjusted instead of adjusting the time interval after the trigger is generated.

The timeout timer is checked to see if it has counted down (reached a value of zero) in step 318. If the timeout timer has counted down, the timeout timer forces the virtual trigger to a count of zero at step 320 and the Heart Rate routine is exited. If the timeout timer has not fully counted down to zero, then the virtual trigger timer is checked at step 334. If the virtual trigger timer has not counted down to zero, then the Heart Rate routine is exited at step 322. Alternatively, if the virtual trigger timer has counted down to zero, then the virtual trigger timer is set to the pulse period in step 332. After resetting the timer to the pulse period in step 336, the virtual trigger is issued to the Heart Rate Checking routine in step 338. The Heart Rate Checking Routine is illustrated in the flowchart shown in FIG. 3C.

Referring to FIG. 3C, the Heart Rate Checking routine checks for the occurrence of the virtual trigger at step 342. If a virtual trigger has occurred, the Heart Rate Routine checks the elapsed time since the last virtual trigger occurred at step 344. If the elapsed time is less than the minimum internal time limit, typically around 200 milliseconds, the virtual trigger is marked as a false virtual trigger at step 346. If the elapsed time is greater than the minimum limit, than the routine calls the heart rate qualification routine at step 348. After calling the heart rate qualification routine the Heart Rate Checking routine is exited at step 350.

The detected optical signal waveform is typically sampled at a rate of 57 samples per second. When the digitized red and infrared signals for a given portion of detected optical signals are obtained, they are stored in a buffer called DATBUF and a software flag indicating the presence of data is set at step 356. This set flag calls a pulse detection routine at step 358. The pulse detection routine processes each new digitized optical signal waveform sample and is called once per data point. The pulse detection routine determines pairs of maximum and minimum amplitudes for the detected signal data and presents the pairs to a pulse qualification routine shown at step 362 for processing. The Heart Rate Level 3 routine evaluates a pair of maximum and minimum amplitudes for the detected signal data, uses conventional techniques for evaluating whether a detected pulse is acceptable for processing and performs the blood oxygen saturation calculation on accepted pulses.

Figure 3E:
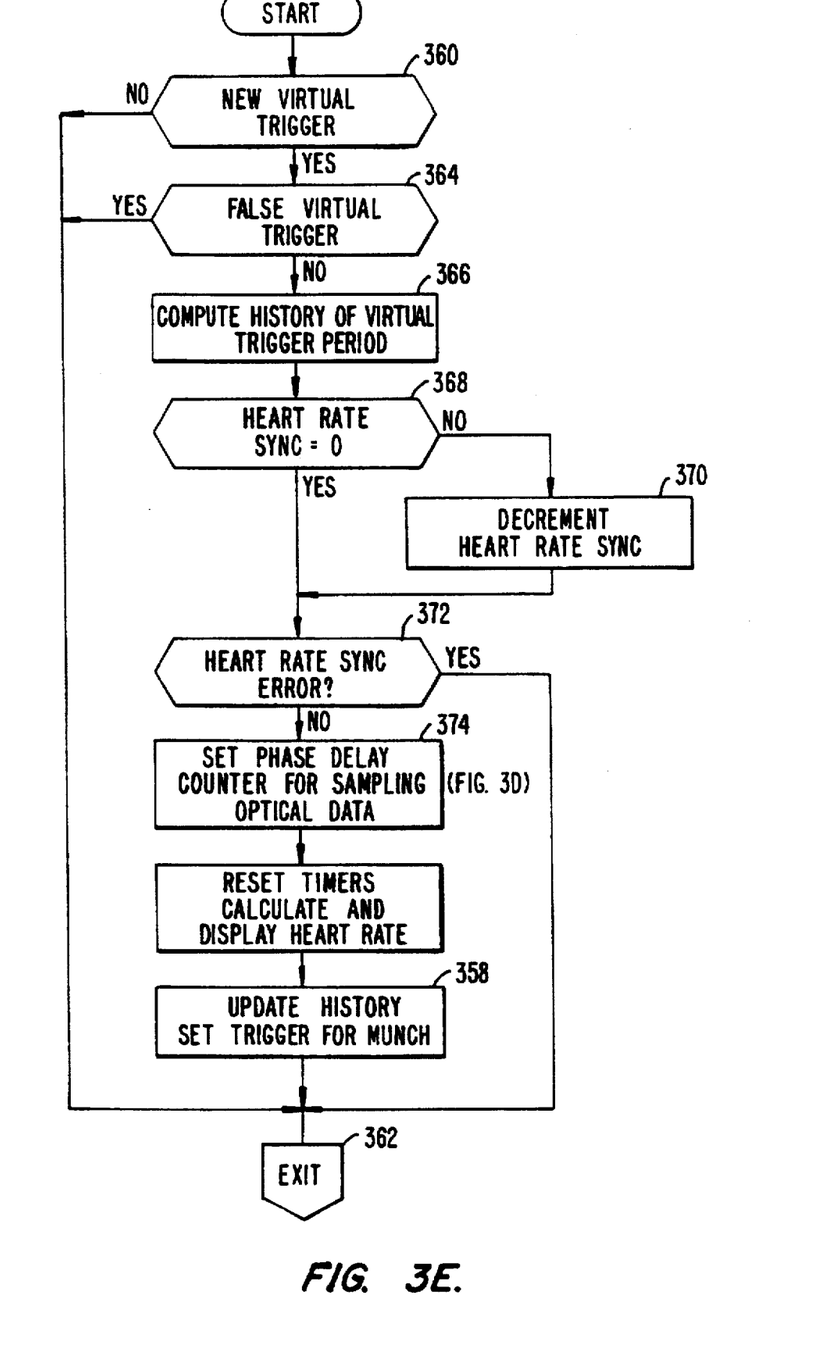

The Heart Rate qualification routine (FIG. 3E) validates the heart rate periods against previous heart rater periods before enabling the C-lock process. In addition, the Heart Rate qualification routine maintains the ensemble averaging buffer pointers and resets them as necessary, displays the heart rate, updates the history buffers and sets the trigger for the pulse detection routine to calculate pulse oximetry data for determining oxygen saturation based on the updated ensemble averaging buffer data at step 358. Referring to FIG. 3E, the Heart Rate pulse qualification routine checks to see if a new virtual trigger has occurred at step 360. If a new virtual trigger has not occurred, the routine is exited at step 362. If a virtual trigger is detected, the routine checks to see if it is a false virtual trigger at step 364. If the virtual trigger data is correct, then a history of the virtual trigger period is computed at step 366.

After computing the history, the Heart Rate qualification routine checks to see if the heart rate signal is synchronized at step 368. The heart rate signal is synchronized after receiving a predetermined number, typically five, virtual triggers. The pulse qualification routine tests the heart rate synch counter at step 368. If the heart rate synch counter is greater than 0, the heart rate signal is determined not to be in synchronization and the heart rate synch counter is decremented by one at step 370. Thus, when the heart rate synch counter is at 0 at step 368 indicating that the required number of synchronized heart rate signals has occurred, then it is determined that there is heart rate synchronization.

The saturation calculation will be based upon the ensemble averaging buffer data only after five virtual triggers have passed in synch and the synchronization flag is raised. Loss of synchronization resets the heart rate synch counter to 5. Whether or not there is heart rate synchronization, the virtual trigger is checked against the pulse history at step 372. If an error exists, the Heart Rate qualification routine is exited. If an error does not exist, then the routine starts a phase delay timer/counter at step 374. The purpose of the phase delay counter is to ensure that the optical signal data is placed into the beginning of the ensemble averaging buffer at a point in time such that it will add in phase to the composite pulse previously stored in the ensemble averaging buffer.

The C-Lock process described in U.S. Pat. Nos. 4,911,167 and 4,928,692 relies on a specific events in time (occurrence of the R-wave of the ECG waveform) to filter out artifact asynchronous to the optical pulse. In actuality, the effectiveness of C-Lock is not dependent on the specific phase relationship between the ECG triggers and the optical pulses. When the heart rates are regular, the C-Lock process is similar to application of an analog comb filter to the optical pulse. The analog comb filter is not event-dependent, but is frequency-dependent to the optical signal.

Figure 4A:
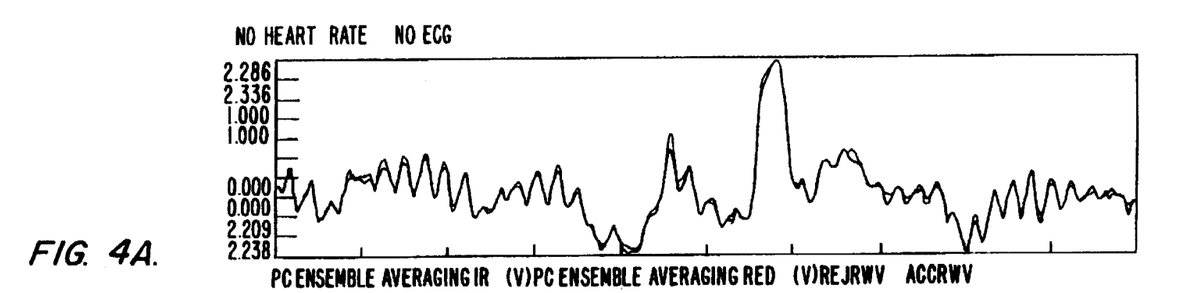
FIGS. 4A, 4B and 4C illustrate a graphical representation of blood flow characteristics where no heart rate signal and no ECG signal is available to implement the C-Lock process.
Figure 4B:
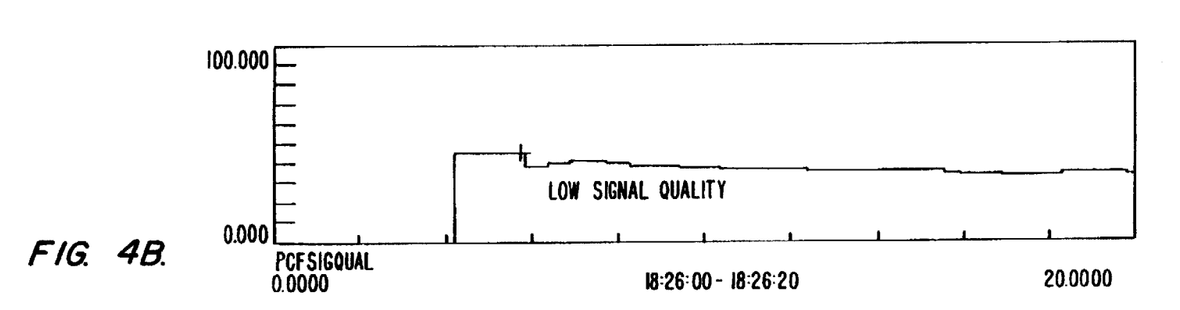
Figure 4C:
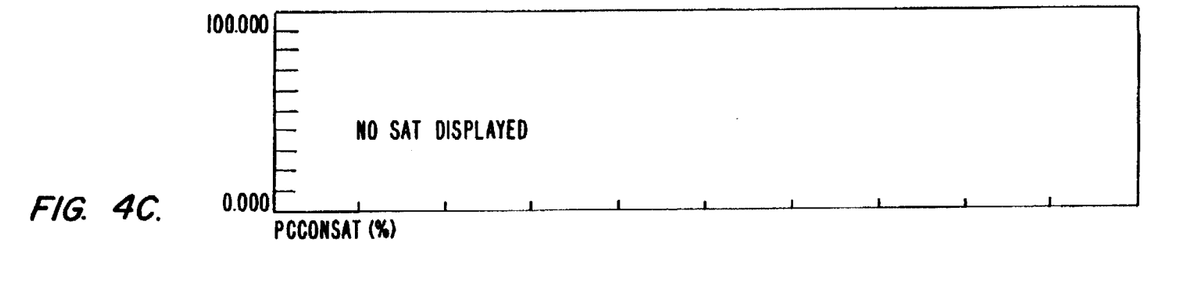

FIGS. 4A, 4B, and 4C illustrate a graphical representation of blood flow characteristics in an embodiment where no heart rate signal and no ECG signal is available to implement the C-Lock process. Specifically, FIG. 4A illustrates the ensemble averaging waveform which represents optical signal data in the ensemble averaging buffer over the designated time period. The Y axis represents the voltage of the optical signal. Because no ECG or heart rate signal is available, the C-Lock process is not implemented and thus the ensemble averaging waveform susceptibility to motion artifact is increased. Because no C-Lock implementation occurs, the signal quality is poor as can be seen in FIG. 4B. Referring to FIG. 4B, the Y axis represents the signal quality on a scale from 0 to 100. Because the signal quality is poor, as can be seen in FIG. 4C, no saturation signal is displayed. The Y axis of FIG. 4C represents saturation on a scale of 0 to 100 over the designated time period.

Figure 5A:
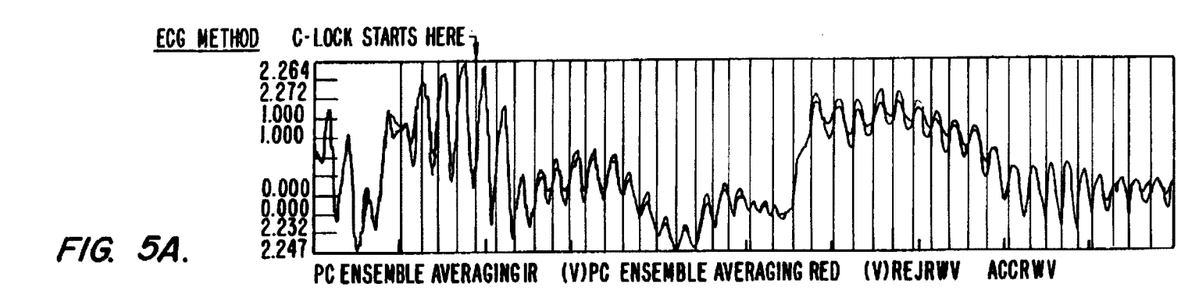
FIGS. 5A, 5B and 5C illustrate a graphical representation of blood flow characteristics when an ECG signal is available to implement the C-Lock process.
Figure 5B:
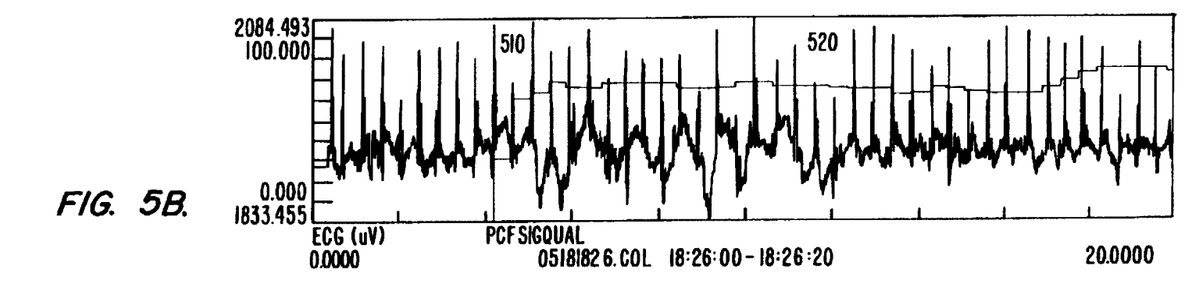
Figure 5C:
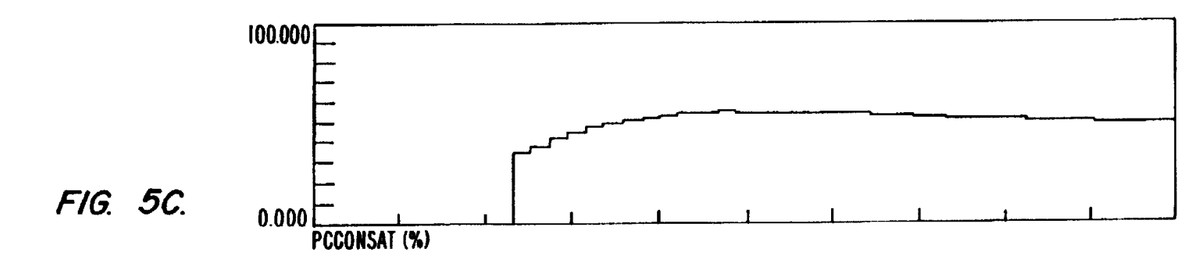

FIGS. 5A through 5C correspond to the signal data represented in FIGS. 4A through 4C except that an ECG signal is available in order for implementing the C-Lock process. FIG. 5B illustrates both an ECG waveform 510 and a signal quality signal 520. The ECG waveform is represented in microvolts and ranges from 1800 microvolts to 2,100 microvolts. The signal quality 520 ranges in value from 0 to 100. The signal quality value 520 is much higher than that shown in corresponding FIG. 4B where no ECG signal is available to implement C-Lock. Because the signal quality is high, the saturation value can be calculated as is shown in FIG. 5C.

Figure 6A:
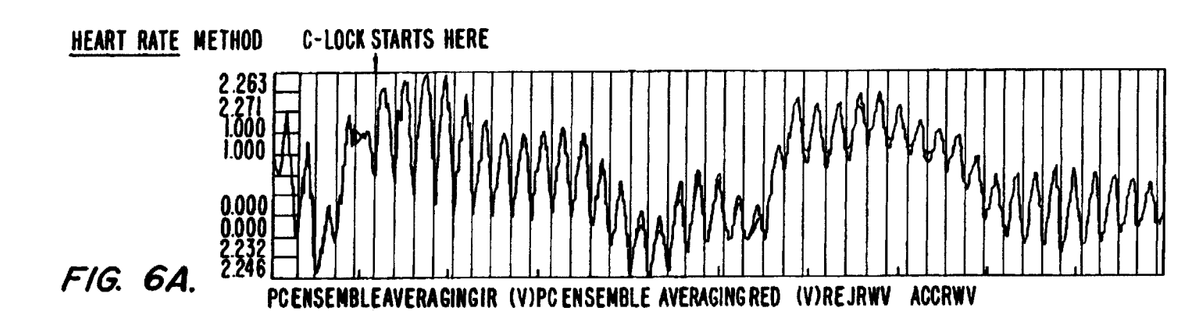
FIGS. 6A, 6B and 6C illustrate a graphical representation of blood flow characteristics where a heart rate signal is used to trigger data collection according to the present invention.
Figure 6B:
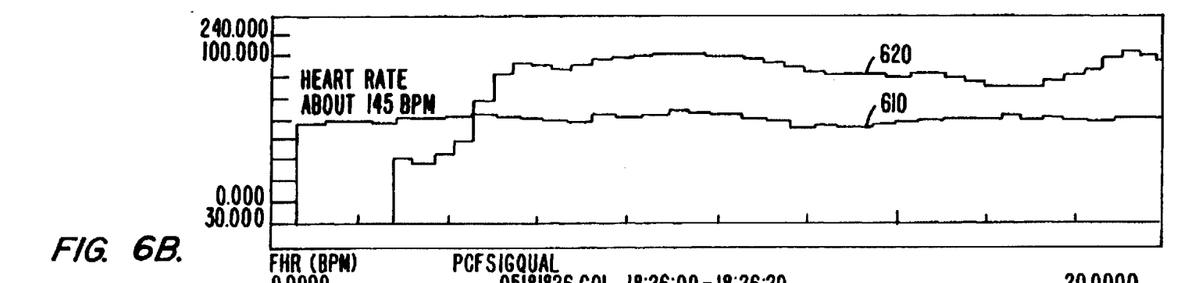
Figure 6C:
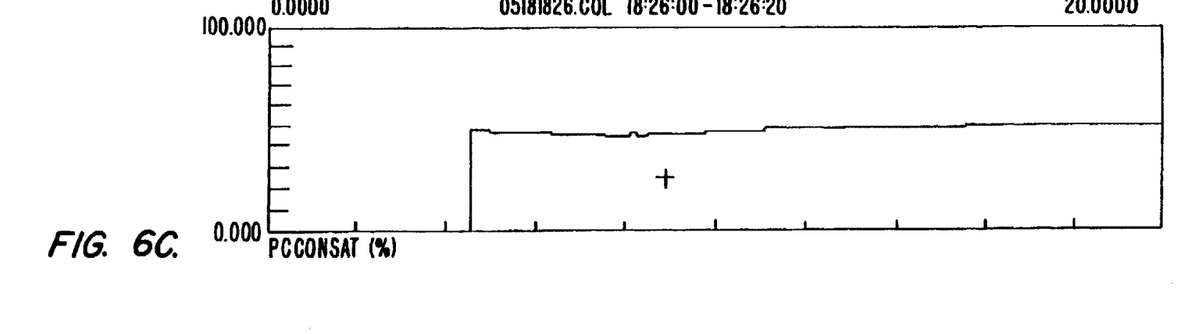

FIGS. 6A through 6C correspond to the signal data represented in FIGS. 4A through 4C and 5A through 5C except that a heart rate signal is used to implement the C-Lock process. FIG. 6B illustrates both a heart rate signal 610 and a signal quality signal 620. Because use of the heart rate signal to implement C-Lock results in a high signal quality (FIG. 6B), the saturation value can be calculated as is shown in FIG. 6C.

There are times when the pulse oximetry system computes an incorrect heart rate from high level ECG R-wave triggers it is receiving, yet the heart rate monitor reports an accurate heart rate. At these times, the pulse oximetry system computes a low signal quality and does not display oxygen saturation. Implementing the C-Lock process using the heart rate to determine a virtual trigger should eliminate this artifact and allow a higher signal quality to be computed, resulting in fewer dropouts of the displayed saturation signal. While the pulse oximetry system may reject some ECG triggers when there is some artifact in the ECG and thus fail to issue a trigger for the C-Lock process, using a heart rate to generate a virtual trigger should allow for several accurately timed triggers to be issued in the event the heart rate is not accurately updated every beat. This implementation of C-Lock has been simulated using a personal computer for over a hundred cases for which only an external fetal heart rate was available and has been observed to as much double the amount of time the oximetry system can report a high signal quality saturation, as compared to a pulse oximetry system which does not have external heart rate available to it.

As will be understood by those familiar with the art, the present invention may be embodied in other specific forms without departing from the spirit or essential characteristics thereof. The heart rate signal could either be a representation of the frequency of the heart rate, or the raw signal itself which has to be processed to determine the frequency. The heart rate signal can come either from a Doppler ultrasound technique, from monitoring blood pressure, from impedance imaging, acoustically through a stethoscope, or by any other mechanism. The heart rate can be derived from the same site on the patient as the oximeter probe, or from a completely different site. The processing using the virtual trigger can either be real time or after the recorded data is stored on a disk, and could be done in hardware or software.

The data from the oximeter could be processed as soon as it is stored in RAM 224 of FIG. 2B. Alternately, a large amount of data could be off-loaded to a separate disk, and the processing could retrieve the data from the disk in a non-real-time operation. The oximetry signal itself could be generated from any type of oximeter probe, and could be a probe which uses two or three wavelengths, for instance.

The process of the present invention could be used for other physical phenomena than oxygen saturation or even blood flow. In some instances, the periodic information may be undesirable, and may be suppressed by using the virtual trigger process of this invention, rather than being enhanced. In addition, instead of the maximum and minimum values of the periodic oximeter signal being processed, the entire waveform could be processed to determine oxygen saturation or other characteristics. Accordingly the disclosure of the preferred embodiment is intended to be illustrative, but not limiting, the scope of the invention which is set forth in the following claims.

```
//FHR = Fetal Heart Rate, from external monitor
// Global Variables
unsigned int EnableFHRTriggers = 0;
unsigned int EnableFHRSink = 0
unsigned int Fhr;
unsigned int FHRPeriod = 0
void *UseFHRTimer=NULL;
void DontUseFHR(void);
//Initialization to parse heart rate data from input files,
//Timer creation, flags set
        EnterSubMsgHandler(MONITOR, FetalMonitorSink);
        EnableFHRSink = 1;
        UseFHRTimer = CreateTimer(Intermittent, DontUseFHR);
        EnableFHRTriggers = 1;
// Called when heart rate updated
void FetalMonitorSink(void *DataPtr)
{
    static unsigned int FhrFraction;
    static unsigned int LastFhrFraction;
```

```
            static unsigned int LastFhr;
            static unsigned int LastFhrPeriod;
            if (EnableFHRSink)
            {
                Fhr = (unsigned) (*((unsigned char *)DataPtr+1));
                FhrFraction = (unsigned) (*((unsigned char *)DataPtr));
            }
            if (Fhr > 0)
            {
                if (EnableFHRTriggers
    // Has heart rate changed, or was an old value sent instead?
    // It is virtually guaranteed that a human heart rate will change by at
    // least 1 Beat Per Minute within a few heartbeats.
                    if ((LastFhrFraction != FhrFraction) || (LastFhr != Fhr))
    // Ignore values out side of the 30-240 BPM range, as they can't be real
                    { if ((Fhr >= 30) && (Fhr <= 250))
                        { UseFhr = 1
    // Continue to issue triggers based on this rate for no more than 5 seconds
                            SetTimer(UseFHRTimer, TimeToTicks (FIVESEC));
                            FHRPeriod = TimeToTicks(SIXTYSEC/Fhr);
    // Adjust the virtual trigger timer to issue next trigger based on current
    // heart rate, even though it had already been set based on the previous
    // heart rate
                            if (LastFhrPeriod > 0)
                                TicksUntilFHRTrigger += (FHRPeriod - LastFhrPeriod);
    // Make sure the timer doesn't go negative due to the adjustment
                            if ((int)TicksUntilFhrTrigger < 0)
                                TicksUntilFhrTrigger = 0
                        }
                    }
    // Save heart rate in order to see if it gets updated next time
                LastFhr = Fhr;
                LastFhrFraction = FhrFraction;
                LastFhrPeriod = FHRPeriod;
            }
    //Every time optical data is received, check if time to issue new
    //virtual trigger. If time, issue trigger, initiate qualification
    //of trigger, and reset virtual trigger timer. Decrement Virtual
    //Trigger Timer. Qualification of triggers and all subsequent processing
    //uses the same algorithm (and code) as that used with R-wave triggers
    //from ECG
            if (EnableFHRTriggers)
            { if (FHRPeriod > 0)
                { if (TicksUntilFhrTrigger < 35)
                    {
                        RwvOccur.Data = 1
                        RwvOccur.TimeStamp = OpticalTicks;
                        QualRwv(RwvOccur, FHR);
                        TicksUntilFhrTrigger += FHRPeriod;
                    }
                    TicksUntilFhrTrigger -= 35;
                }
            }
    // The virtual trigger timeout timer calls this routine after 5 seconds
    // if the heart rate is not updated. Once this routine is called, no
    // new virtual triggers will get sent until the heart rate is updated again
            void DontUseFHR(void)
            {
                UseFhr = 0;
                FHRPeriod = 0;//This will signal that the timeout timer has counted
                down.
                TicksUntilFhrTrigger = 0;
            }
```

What is claimed is:

1. An apparatus comprising:

means for generating a first signal from a periodic physical activity;

means for generating a second signal having a first frequency corresponding to said periodic physical activity;

means for generating a trigger having said first frequency, said trigger being generated independent of any waveform feature defining a period of said second signal; and means for processing said first signal in periods defined by said trigger.

2. The apparatus of claim 1 wherein said first signal is a pulse oximeter signal and said second signal is a heart rate signal.

3. The apparatus of claim 2 wherein said heart rate signal is a representation of a heart rate frequency.

4. The apparatus of claim 2 wherein said heart rate signal is a periodic signal, and further comprising means for converting said periodic signal into a representation of said first frequency of said heart rate.

5. The apparatus of claim 2 wherein said heart rate signal is obtained from a different site on a patient than said pulse oximeter signal.

6. The apparatus of claim 1 wherein said means for processing enhances periodic information in said first signal from a plurality of said periods.

7. A method comprising the steps of:

generating a first signal from a periodic physical activity;

generating a second signal having a first frequency corresponding to said periodic physical activity;

generating a trigger having said first frequency, said trigger being generated independent of any waveform feature defining a period of said second signal; and processing said first signal in periods defined by said trigger.

8. The method of claim 7 wherein said first signal is a pulse oximeter signal and said second signal is a heart rate signal.

9. The method of claim 8 wherein said heart rate signal is a representation of a heart rate frequency.

10. The method of claim 8 wherein said heart rate signal is a periodic signal, and further comprising the step of converting said periodic signal into a representation of said first frequency of said heart rate.

11. The method of claim 8 wherein said heart rate signal is obtained from a different site on a patient than said pulse oximeter signal.

12. The method of claim 7 wherein said step of processing enhances periodic information in said first signal from a plurality of said periods.

13. An apparatus comprising:

means for generating a first signal from a periodic physical activity;

means for generating a second signal having a first frequency, said first frequency being synchronized with said periodic physical activity; and means for filtering the first signal, said filtering means being characterized by said first frequency, and being independent of any waveform feature defining a period of said second signal.

14. A method comprising the steps of:

generating a first signal from a periodic physical activity;

generating a second signal having a first frequency, said first frequency being synchronized with said periodic physical activity; and filtering the first signal with a filter characterized by said first frequency and being independent of any waveform feature defining a period of said second signal.

* * * * *